(12) United States Patent
Sherman

(10) Patent No.: US 6,740,340 B1
(45) Date of Patent: May 25, 2004

(54) PHARMACEUTICAL TABLETS COMPRISING AN NSAID AND A PROSTAGLANDIN

(75) Inventor: Bernard Charles Sherman, 50 Old Colony Rd., Willowdale, Ontario (CA), M2L 2K1

(73) Assignee: Bernard Charles Sherman, Toronto (CA)

( * ) Notice: Subject to any disclaimer, the term of this patent is extended or adjusted under 35 U.S.C. 154(b) by 0 days.

(21) Appl. No.: 09/719,142

(22) PCT Filed: Jun. 10, 1999

(86) PCT No.: PCT/CA99/00541

§ 371 (c)(1),
(2), (4) Date: Dec. 8, 2000

(87) PCT Pub. No.: WO99/65496

PCT Pub. Date: Dec. 23, 1999

(30) Foreign Application Priority Data

Jun. 15, 1998 (CA) .............................................. 2241342

(51) Int. Cl.[7] .............................. A61K 9/20; A61K 9/22; A61K 9/28

(52) U.S. Cl. ........................ 424/468; 424/464; 424/465; 424/474

(58) Field of Search ................................. 424/472, 475, 424/464, 465, 474, 468; 514/54

(56) References Cited

U.S. PATENT DOCUMENTS

| | | | | | |
|---|---|---|---|---|---|
| 5,232,704 A | * | 8/1993 | Franz et al. | ................. | 424/456 |
| 5,288,507 A | * | 2/1994 | Sims et al. | ................. | 424/682 |
| 5,523,321 A | * | 6/1996 | Stuerzebecher et al. | .... | 514/469 |
| 5,601,843 A | * | 2/1997 | Gimet et al. | ................. | 424/475 |
| 5,935,939 A | * | 8/1999 | Kararli et al. | ................. | 514/54 |

FOREIGN PATENT DOCUMENTS

| | | |
|---|---|---|
| DE | 196 37 479 A1 | 9/1996 |
| EP | 0864 324 A1 | 3/1998 |
| WO | WO 98/10752 | 3/1998 |

* cited by examiner

*Primary Examiner*—James M. Spear
(74) *Attorney, Agent, or Firm*—Neil H. Hughes; Ivor M. Hughes; Marcelo K. Sarkis

(57) ABSTRACT

A pharmaceutical tablet which incorporates two smaller tablets, one of which comprises an NSAID and the other of which comprises misoprostol.

11 Claims, No Drawings

PHARMACEUTICAL TABLETS COMPRISING AN NSAID AND A PROSTAGLANDIN

BACKGROUND OF THE INVENTION

The invention herein is directed to a pharmaceutical tablet which comprises both an NSAID and misoprostol.

Nonsteroidal anti-inflammatory drugs (NSAIDs) comprise a class of drugs which have long been recognized as having high therapeutic value especially for the treatment of inflammatory conditions such as exhibited in inflammatory diseases like osteoarthritis and rheumatoid arthritis. While the NSAIDs present a beneficial therapeutic value, they also exhibit undesirable side effects. An especially undesirable side effect of the administration of NSAIDs is the ulcerogenic effects generally associated with chronic use. NSAID induced ulcers in the stomach can be dangerous. Such ulcers generally exhibit few or no symptoms and may cause dangerous bleeding when undetected. In some instances, bleeding ulcers can prove fatal.

Certain prostaglandins have been shown to prevent NSAID induced ulcers. Misoprostol is a prostaglandin which has been accepted for use in the treatment of NSAID induced ulcers in many countries, including the United States.

It is desirable to provide a pharmaceutical composition which exhibits the beneficial properties of an NSAID and which also exhibits the beneficial properties of misoprostol for countering the ulcerogenic side effects attendent to NSAID administration.

This can be achieved by combining an NSAID and misoprostol in a single pharmaceutical tablet. However this in not easy to do, because misoprostol is highly unstable, and it is thus desirable not to have the misoprostol and NSAID mixed together, so as to prevent any deleterious effect of the NSAID on the stability of the misoprostol.

One solution to this problem, which is disclosed in U.S. Pat. No. 5,601,843, is to produce a tablet consisting of an inner core which comprises the NSAID and a mantle which surrounds the inner core and comprises the misoprostol. It is also disclosed that, in order to prevent contact between the misoprostol and the NSAID at the surface of the inner core, the inner core may be coated with an inert coating. Such coating may be an enteric coating, which also serves to reduce the likelihood of the NSAID dissolving in the stomach and thereby prevent exposing the stomach to the NSAID.

While the invention of U.S. Pat. No. 5,601,843 accomplishes its objective of separating the NSAID from the misoprostol, it has certain disadvantages. One disadvantage is the need to have a coating on the inner core in order to completely prevent contact between the NSAID in the inner core and the misoprostol in the mantle.

A second disadvantage is that the misoprostol is dispersed throughout the mantle, and is thus exposed to the environment at the surface of the tablet. This exposure increases the vulnerability of the misoprostol to degradation due to the effects of light or atmospheric oxygen and moisture.

The object of the present invention is to enable a pharmaceutical tablet that incorporates both an NSAID and misoprostol, but overcomes these disadvantages.

BRIEF SUMMARY OF THE INVENTION

The present invention is a pharmaceutical composition in the form of a tablet in which two smaller tablets are embedded, one of which comprises an NSAID and the second of which comprises misoprostol.

DETAILED DESCRIPTION OF THE INVENTION

Pharmaceutical tablets are routinely made on a tablet press. In the tabletting process, a mixture of materials in the form of a free flowing powder or granular mix is filled into a metal die, into which a metal punch protrudes from beneath. A second metal punch is then inserted into the die from above, and pressure is applied to the upper and lower punches to cause the powder or granular mix to be compressed into a tablet. The upper punch is then withdrawn, and the tablet is ejected from the die by raising the lower punch further into the die.

Compositions (i.e. tablets) of the present invention may be made as follows:

1. Firstly, a tablet comprising the NSAID and a tablet comprising the misoprostol are made in separate tabletfing operations. The portion of the composition which surrounds the two smaller tablets will be referred to herein as the "shell".
2. Then the final composition is assembled in a further tabletting operation as follows:
   (i) Part of the powder or granular mix of which the shell is to be comprised is filled into the die, into which a punch has been inserted from below.
   (ii) One of the smaller tablets comprising the NSAID and one of the smaller tablets comprising the misoprostol are then inserted into the die.
   (iii) The balance of the powder or granular mix of which the shell is to be comprised is then filled into the die to cover two smaller tablets.
   (iv) The upper punch is then inserted into the die from above and pressure is applied between the punches to compress the powder or granular mix around the two smaller tablets into the form of the final tablet.
   (v) The upper punch is then withdrawn and the lower punch is raised further into the die to eject the composition.

The NSAID contained within one of two smaller tablets will preferably be piroxicam or diclofenac or a salt of diclofenac such as diclofenac sodium or diclofenac potassium. Most preferably, the NSAID will be diclofenac sodium.

Where diclofenac or a salt thereof is used, the amount per tablet will preferably be from 25 to 75 mg. The tablet containing diclofenac or salt thereof will contain, along with the diclofenac or salt thereof, usual tablet excipients such as binders, lubricants, fillers and the like. Preferably, the tablet containing the diclofenac or salt thereof will be coated with an enteric film coating to prevent the diclofenac or salt thereof from dissolving until after it has passed through the stomach and entered the small intestine. The enteric coating can be formulated with any suitable enteric coating polymer, many of which are known to those skilled in the art.

Where piroxicam is used as the NSAID, the amount per tablet will preferably be 10 to 20 mg. Again the tablet containing piroxicam will also comprise usual tablet excipients.

The tablet containing the misoprostol will also include, along with the misoprostol, usual tabletting excipients. The misoprostol will preferably be used in the form of a dispersion in hydroxypropyl methylcelulose, which is known in the prior art to improve the stability of misoprostol. The quantity of misoprostol per tablet will preferably be about 200 μg.

The shell which surrounds the tablet containing the NSAID and the tablet containing the misoprostol will be comprised of usual tablet excipients, without any active medicinal ingredient mixed therein.

The invention will be further understood from the following example, which is intended to be illustrative and not limiting of the scope of the invention.

EXAMPLE 1

Tablets containing diclofenac sodium are made with a composition as follows:

|  | Amount per tablet |
| --- | --- |
| Diclofenac sodium | 50.0 mg |
| Microcrystalline cellulose | 24.0 mg |
| Magnesium stearate | 1.0 mg |
| Croscarmellose sodium | 5.0 mg |
|  | 80.0 mg |

These cores are then optionally enteric coated by spraying onto them a suspension or solution of an enteric coating polymer and a plasticizer.

EXAMPLE 2

Tablets containing misoprostol are made with a composition as follows:

|  | Amount per tablet |
| --- | --- |
| Misoprostol 1% dispersion in hydroxypropyl methylcellulose | 20.0 mg |
| Microcrystalline cellulose | 8.5 mg |
| Magnesium stearate | 0.5 mg |
| Croscarmellose sodium | 1.0 mg |
|  | 30.0 mg |

EXAMPLE 3

A powder mix for producing the shell of the final tablet is prepared as a mixture of 99.5% by weight microcrystalline cellulose and 0.5% magnesium stearate.

EXAMPLE 4

The final composition is then made by making tablets from the mix of Example 3 and embedding in each such tablet one tablet from Example 1 and one tablet from Example 2, by the procedure previously described; that is to say, using a tablet press equipped to insert one tablet from Example 1 and one tablet from Example 2 as well as a quantity of the powder mix for the shell from Example 3 into a die, and making the final tablet by compression between a lower punch and a upper punch inserted into the die from below and above respectively.

What is claimed is:

1. A pharmaceutical tablet comprising a shell in which is imbedded two smaller tablets covered by the material of the shell of the pharmaceutical tablet, one of which smaller tablets comprises an NSAID and the other of which smaller tablets comprises misoprostol, whereby the two smaller tablets are not exposed to the environment at the surface of the pharmaceutical tablet, being protected by said shell.

2. The pharmaceutical tablet of claim 1 wherein the smaller tablet containing the NSAID is enteric coated.

3. A pharmaceutical tablet as in claim 1 or 2 wherein the NSAID is piroxicam.

4. A pharmaceutical tablet as in claim 1 or 2 wherein the NSAID is selected from diclofenac and salts thereof.

5. A pharmaceutical tablet as in claim 3 wherein the amount of piroxically is from about 10 mg to about 20 mg.

6. A pharmaceutical tablet as in claim 4 wherein the amount of diclofenac or a salt thereof is from about 25 mg to about 75 mg.

7. The pharmaceutical tablet of claim 1 or 2 wherein the amount of misoprostol is about 200 µg.

8. The pharmaceutical tablet of claim 3 wherein the amount of misoprostol is about 200 µg.

9. The pharmaceutical tablet of claim 4 wherein the amount of misoprostol is about 200 µg.

10. The pharmaceutical tablet of claim 5 wherein the amount of misoprostol is about 200 µg.

11. The pharmaceutical tablet of claim 6 wherein the amount of misoprostol is about 200 µg.

* * * * *